(12) United States Patent  (10) Patent No.: US 8,639,520 B2
Finn et al.  (45) Date of Patent: Jan. 28, 2014

(54) SYSTEM AND METHOD FOR CREATING A VISUALIZATION INDICATING RELATIONSHIPS AND RELEVANCE TO AN ENTITY

(75) Inventors: Christopher S. Finn, Liberty, MO (US); Steven S. Crooks, Gladstone, MO (US); David P. McCallie, Jr., Stilwell, KS (US); David J. O'Larte, Peculiar, MO (US)

(73) Assignee: Cerner Innovations, Inc., Kansas City, KS (US)

( * ) Notice: Subject to any disclaimer, the term of this patent is extended or adjusted under 35 U.S.C. 154(b) by 2195 days.

(21) Appl. No.: 10/860,458

(22) Filed: Jun. 2, 2004

(65) Prior Publication Data

US 2005/0076060 A1   Apr. 7, 2005
US 2011/0004529 A2   Jan. 6, 2011

Related U.S. Application Data

(60) Provisional application No. 60/509,003, filed on Oct. 6, 2003, provisional application No. 60/546,935, filed on Feb. 23, 2004.

(51) Int. Cl.
  *G06Q 10/00*  (2012.01)
  *G06Q 50/00*  (2012.01)
(52) U.S. Cl.
  USPC .............................................................. 705/2
(58) Field of Classification Search
  USPC .......................................................... 705/2, 3
  See application file for complete search history.

(56) References Cited

U.S. PATENT DOCUMENTS

| | | | | |
|---|---|---|---|---|
| 5,495,567 | A | * | 2/1996 | Iizawa et al. .................. 715/762 |
| 5,835,758 | A | * | 11/1998 | Nochur et al. ................ 707/102 |
| 6,073,138 | A | * | 6/2000 | de l'Etraz et al. ............. 707/748 |
| 6,154,750 | A | * | 11/2000 | Roberge et al. ............ 707/104.1 |
| 6,505,202 | B1 | * | 1/2003 | Mosquera et al. ............. 707/10 |
| 7,379,880 | B1 | * | 5/2008 | Pathria et al. ................. 705/1.1 |
| 7,451,096 | B2 | * | 11/2008 | Rucker ............................. 705/3 |
| 2001/0049681 | A1 | * | 12/2001 | Bova .............................. 707/10 |

(Continued)

OTHER PUBLICATIONS

Sager et al., "Natural Language Processing and the Representation of Clinical Data," *Journal of the American Medical Informatics Association*, vol. 1, No. 2, Mar./Apr. 1994, pp. 142-160.

(Continued)

*Primary Examiner* — John Pauls
*Assistant Examiner* — Trang Nguyen
(74) *Attorney, Agent, or Firm* — Shook, Hardy & Bacon L.L.P.

(57) ABSTRACT

A system and method for generating interactive visualizations of clinical relationships is provided. The method includes determining what entities have had some clinical contact with an entity of interest and collecting data regarding each entity and each entity's contacts with the entity of interest. The collected data can be filtered to remove unwanted entities and properties. Algorithms are applied to generate clinical relevance scores, which represent the relationship between the entities and the entity of interest. In addition, each entity is assigned components that allow for some executable behavior when an entity is selected in a display. Finally, the appropriate visualization is selected and a display of the relationships is generated.

26 Claims, 5 Drawing Sheets

(56) References Cited

U.S. PATENT DOCUMENTS

| | | | |
|---|---|---|---|
| 2002/0133392 A1* | 9/2002 | Angel et al. | 705/10 |
| 2002/0169737 A1* | 11/2002 | Armstrong et al. | 706/59 |
| 2002/0194022 A1* | 12/2002 | Comite | 705/2 |
| 2003/0130973 A1* | 7/2003 | Sumner et al. | 706/45 |
| 2004/0093331 A1* | 5/2004 | Garner et al. | 707/3 |
| 2004/0122803 A1* | 6/2004 | Dom et al. | 707/3 |
| 2004/0153436 A1* | 8/2004 | Pope et al. | 707/1 |
| 2004/0177071 A1* | 9/2004 | Massey et al. | 707/7 |
| 2004/0249821 A1* | 12/2004 | Nies et al. | 707/100 |
| 2005/0015381 A1* | 1/2005 | Clifford et al. | 707/100 |
| 2005/0038671 A1* | 2/2005 | Naeymi-Rad et al. | 705/2 |

OTHER PUBLICATIONS

Friedman, et al., "A General Natural-Language Text Processor for Clinical Radiology," *Journal of the American Medical Informatics Association*, vol. 1, No. 2, Mar./Apr. 1994, pp. 161-174.

Cawsey et al., "Natural Language Generation in Health Care," *Journal of the American Medical Informatics Association*, vol. 4, No. 6, Nov./Dec. 1997, pp. 473-482.

Lovis et al., Evaluation of a Command-line Parser-based Order Entry Pathway for the Department of Veterans Affairs Electronic Patient Record, *Journal of the American Medical Informatics Association*, vol. 8, No. 5, Sep./Oct. 2001, pp. 486-498.

* cited by examiner

| | | |
|---|---|---|
| PAIGE KAEDING, RN<br>AVAILABLE<br>LAST TOUCH: 2 HRS AGO | JONATHAN BILLINGS, MD<br>ONLINE<br>LAST TOUCH: 6 HOURS AGO | LEELA COSTAS, LCSW<br>BUSY<br>LAST TOUCH: TUESDAY |
| | | CARL SMITH, RN<br>ONLINE<br>LAST TOUCH: 1 WEEK AGO |
| | LEAH PHELAN, MD<br>AVAILABLE<br>LAST TOUCH: YESTERDAY | D.J. PAPPIS, MD<br>UNAVAILABLE<br>LAST TOUCH: TWO WEEKS AGO |
| RS CONROY, RN<br>UNAVAILABLE | | S. GORMAN, RN<br>UNAVAILABLE<br>LAST TOUCH: 2 WEEKS AGO |
| WILLIAMS ROBERTS, PT<br>ONLINE<br>LAST TOUCH: MONDAY | VIJAY RAMA, MD<br>BUSY<br>LAST TOUCH: 1 WEEK AGO | SUE SMITH, RD<br>ONLINE<br>LAST TOUCH: 1 MONTH GO |

| WEB OF CARE FOR: CHARLES KRAMER (OFFLINE) | | | | |
|---|---|---|---|---|
| NAME | PRESENCE | ROLE | CLINICAL RELEVANCE | LAST TOUCH |
| PAIGE KAEDING | ONLINE | RN | 99 | 2 HRS AGO |
| JOE DECKER | BUSY | ADMITTING MD | 90 | YESTERDAY |
| RS CONROL | AVAILABLE | RN | 45 | 6 HRS AGO |
| LEAH PHELAN | OFFLINE | MD | 22 | LAST YEAR |
| LEELA COSTAS | ONLINE | LCSW | 11 | 2 WKS AGO |

FIG. 6.

SYSTEM AND METHOD FOR CREATING A VISUALIZATION INDICATING RELATIONSHIPS AND RELEVANCE TO AN ENTITY

CROSS-REFERENCE TO RELATED APPLICATIONS

This application claims the benefit of U.S. Provisional Patent Application Ser. No. 60/509,003, filed Oct. 6, 2003 and U.S. Provisional Patent Application Ser. No. 60/546,935 filed Feb. 23, 2004.

STATEMENT REGARDING FEDERALLY SPONSORED RESEARCH OR DEVELOPMENT

Not applicable.

TECHNICAL FIELD

The present invention relates generally to the field of computer software. More particularly, the present invention relates to a computerized system and method for creating interactive visualizations of all entities that have established some form of contact or relationship with an entity of interest.

BACKGROUND OF THE INVENTION

When a person enters a health system, he or she will frequently come in contact with dozens of providers, clinicians, staff members and other patients or persons during the course of care. Healthcare providers often have a need to determine, during this course of care, the care the person has received and who provided that care. In the healthcare industry, this information can be recorded on various forms manually, or can be housed within a computerized clinical information system. Various people within the healthcare system may also need to determine which person has the most relevant information about a particular patient. However, it may be difficult to determine "who knows the patient best." Such information can be gleaned by going through records individually, getting detail about each encounter, and making an estimation of who to contact. However, this process is time consuming, even in an electronic system, and may yield information that ultimately is useless. For example, knowing that a particular nurse is most familiar with a patient may not help solve the immediate need if that nurse is not present or otherwise available.

Likewise, infection control issues may arise in a healthcare setting. In such situations, it is important to identify the persons and resources (rooms, equipment, etc.) that have been exposed to a particular patient. It is also important to know who has subsequently come into contact with those individuals or resources who were exposed to the patient, and the individuals and resources who contacted those individuals and resources exposed to the patient. Again, the information can often be recreated from manual or electronic records, but the process is time consuming and inefficient.

There exists, therefore, a need to quickly and efficiently obtain this kind of information. The information that is needed should also be displayed in a manner that quickly conveys the most relevant information. In addition, it would be advantageous if the display is dynamic and interactive. Most traditional visualizations in the healthcare setting show retrospective views of data specifically stored about the person of interest, often missing the value of dynamic information about relationships that are relevant to the person. However, these visualizations (and the tools associated with these visualizations) do not facilitate real-time, interactive application management during the care process.

Accordingly, there is a need for an efficient system and method for determining the relationship between an entity of interest and the various entities that have had contact with that entity, such as a clinical relationship between a patient and those that have contact with the patient. There is also a need for a system and method for displaying clinical relationship information that allows a user to perform a variety of functions such as viewing and analyzing relationships, initiating collaborative work, and carrying out infection control.

SUMMARY OF THE INVENTION

The present invention generally relates to a system and method for generating interactive visualizations of clinical relationships. The method includes determining entities that have had some clinically-related contact with an entity of interest and collecting data regarding each entity and each entity's contacts with the entity of interest. The collected data can be filtered to remove unwanted entities and properties. Algorithms are applied to generate clinical relevance scores, which represent the relationship between the entities and the entity of interest. In addition, each entity is assigned components that allow for some executable behavior when an entity is selected in a display. Also, the appropriate visualization is selected and a display is generated.

BRIEF DESCRIPTION OF THE SEVERAL VIEWS OF THE DRAWINGS

The present invention is described in detail below with reference to the attached drawing figures, wherein.

DETAILED DESCRIPTION OF THE INVENTION

The present invention is directed to a system and method for creating visualizations representing relationships between various entity elements and an entity of interest. The entity of interest is the focus of the visualization or display. In other words, it is the entity for which care information is generated and visualized. The entity of interest can be a person, such as a patient, a provider, or a caregiver, or can be any inanimate entity, such as a resource (a location, a bed, a room, a piece of equipment, etc.) or other entity. Entity elements are those physical entities that have had some clinical relationship or contact with the entity of interest. An entity element can also be any type of physical entity, either animate or inanimate such as a person or resource capable of having a clinically-related contact with an entity of interest. In one example, discussed below, the entity of interest is a patient in a healthcare setting, and the entity elements are individuals providing various levels of care to that patient. It should be understood, however, that this example is not meant to be limiting and that the invention is applicable to a broad range of entities of interest and entity elements. For instance, a role associated with a class of people is a possible entity element. In this example, a number of different nurses may represented as a single entity element for the nurse role. In a related alternative, a type of resource is a possible entity interest. In this example, a number of x-ray machines may be represented as a single entity element. This is desirable in many clinical situations because the type of resource is oftentimes more relevant to the provision of care than the specific resource such as in the example of an x-ray machine.

Figure 1:
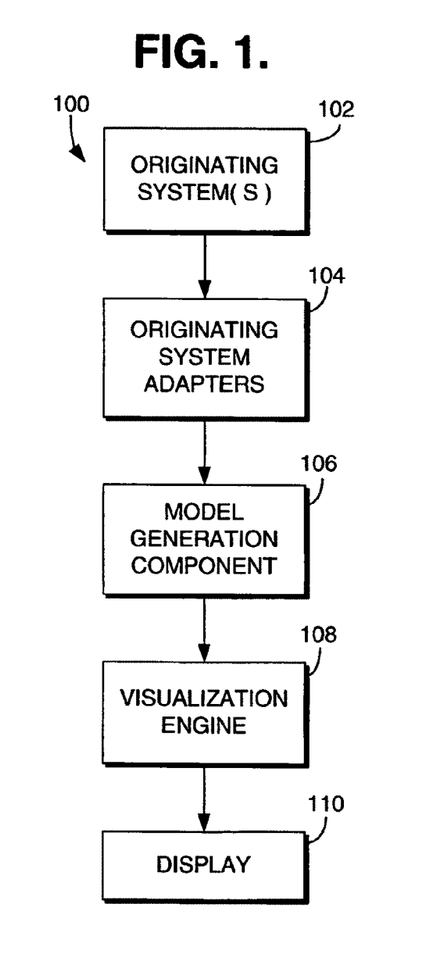
FIG. 1 is a block diagram of a computing system environment suitable for use in implementing the present invention.

FIG. 1 depicts a block diagram of an exemplary computer system 100 for generating and displaying clinical relationships in accordance with the present invention. The system 100 includes various originating systems 102 which provide information to originating system adapters 104. Originating systems are systems that contain potential data used to generate the visualizations discussed below. For example, an originating system could be a clinical data repository, an e-mail system, a presence tracking system, or a financial system. An originating system adapter 104 is provided for each originating system 102 of potential use. A visualization model generation component 106 communicates with the originating system adapters 104. Component 106 takes the data collected by the originating system adapters 104 and manipulates the data using various filters and algorithms as will be described in more detail below. As will also be described below, component 106 generates the collection of information needed to render the desired visualization or display. A visualization engine 108 takes the visualization model generated by component 106 and generates the appropriate visualization for display 110.

Figure 2:
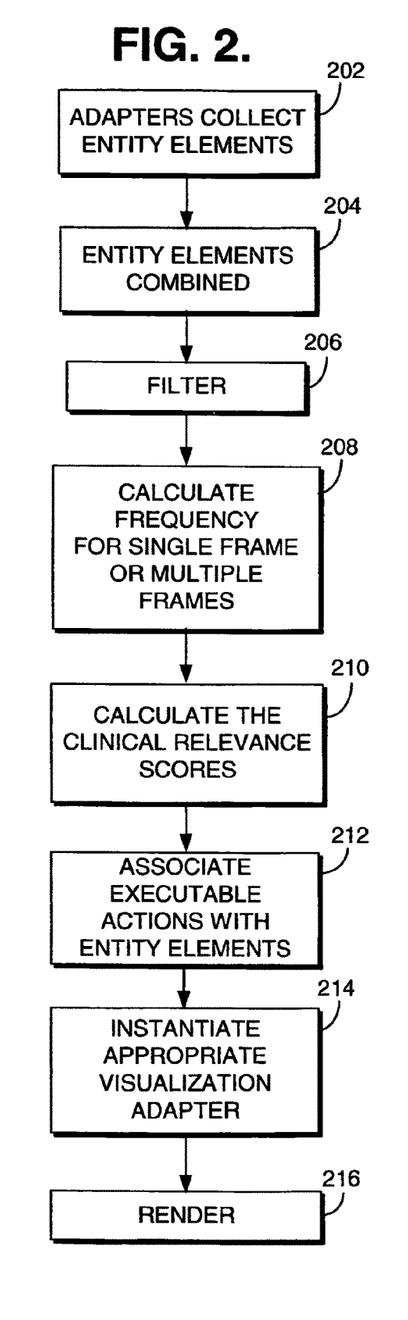
FIG. 2 is a flowchart representative of a computer program for generating and displaying a view of clinical relationships.

The use of the components of FIG. 1 is described in more detail with reference to FIG. 2. The overall method is discussed first and will be followed by an example. The method begins when originating system adapters 104 are invoked to retrieve data from various originating systems 102, as shown at 202. The data retrieved by the adapters 104 are a set of properties (or features) for a given set of entities. This data includes the various entity elements that have had contact (or "touches") with the entity of interest and each entity element's associated properties entity. Entity properties collected from originating systems 102 by adapters 104 may include such things as the entity's name, a unique entity identifier, the primary role of the entity (e.g., attending physician, nurse practitioner, etc.), activity type data, presence status, and generally any other attribute that may be of interest.

Activity types are the data elements indicative of the contact between an entity element and the entity of interest. A contact may be an actual physical contact between an entity element and the entity of interest, a request that will direct a physical contact between an entity element and the entity of interest or a passive contact between the entity of interest and the entity of interest. Examples of actual (or direct) physical contacts include administering a medication to a patient, performing a procedure on a patient and common physical presence of the entity element and entity of interest. If the entity element is a room, piece of equipment or type of equipment, or similar resource, examples of actual physical contact include using a resource for a test or admitting a patient to the resource. Examples of requests that will direct a physical contact between an entity element and the entity of interest include ordering a medication or test, or scheduling a room. Examples of passive (or indirect virtual) contacts include opening a patient's chart, adding a problem to the list of problems for the patient and reviewing an image of the patient.

The presence status property may indicate contact-type information, such as the entity element's current location, online/offline status, availability, and/or device capabilities.

As shown at 204, the retrieved entity elements and properties collected at 202 are combined into a single list and grouped together, or sorted, by entity element. Next, exclusionary filtering is applied to the generated list to remove undesired entities and properties, as shown at 206. In the following step, frequencies are calculated for each activity type or event of interest and are summarized into either a single frame or into multiple frames, as shown at 208. A single frame is used to display a static or "snapshot" view. Multiple frames are used to display a dynamic or "animated" view that can be used to show changes over time, or trends. The frequency information is used in subsequent steps as described below. This frequency information indicates the number of times a particular activity type is encountered. For example, the frequency information can be instructive regarding the number of occasions a particular entity, such as an attending physician, opens the patient's chart. The number of days an entity element interacted with the element of interest is also calculated at this stage. This is sometimes referred to as the number of days "touched." For a particular entity element, such as a doctor, the days touched reflects the number of days the doctor had some interaction with the element of interest, such as the patient.

The next step involves applying clinical relevance algorithms to the data collected to calculate clinical relevance scores for relevance perspectives, as shown at 210. A relevance perspective defines a mathematical function modeling a particular use case. For example, one relevance perspective identifies the most relevant clinical decision maker for a patient. By way of example, a mathematical function for this relevance perspective places a higher value on the number of medication orders or invasiveness of the procedures. Another relevant perspective identifies the caregiver who knows the patient best. A mathematical function for this relevance perspective places a higher value on the number of touches rather than the type of touch. Generally, a clinical relevance algorithm applies a mathematical function against the data collected about particular activity types, including the frequency of such activities, in order to calculate a clinical relevance score. The mathematical function may be a simple linear function or a more complex function applied to the activity type data. The relevance perspectives can either be defaulted by an application for a particular use case, selected by a user from a predefined set of relevance perspectives, or defined by a user by controlling the nature (e.g., weights, constants, terms) of the mathematical function applied against the activity data and activity type data. This step generates a number of relevance perspective vectors, which each contain information about an entity element (including its properties) and a clinical relevance score for a particular relevance perspective. A more specific explanation of the relevance score calculation is set forth in the example below.

As shown at 212, at least one executable action is next associated with each entity element to allow for interactive views. The executable action may be assigned to each entity element. The executable action defines a behavior that occurs when the entity element is acted upon by the user. For example, an executable action could invoke a particular Uniform Resource Locator (URL) to begin a real-time collaboration session with the user. An executable action could also be associated with a Java class file that, when invoked, changed database information associated with the entity element. Likewise, an executable action could be a JavaScript function which, when invoked by the user, changes the nature of the relationship between the entity element and the entity of interest. Following this step, the visualization model for the display is complete. The visualization model includes the collection of relevance perspective vectors, the executable actions associated with entity elements, the associated frames (for animation), and other information necessary for display (either static or animated).

After a visualization model has been generated, the visualization engine 108 generates the display. Different visualization adapters within engine 108 are selected, as shown at 214, and invoked to render the appropriate display, as shown at 216. The visualization engine 108 and generation of visualizations will be described in more detail below.

A wide variety of displays can be generated by the present invention. Because the visualization model and the visualization displays are separate, the displays may be a graphical view or a tabular view. In addition, the displays or visualizations can be separated into families of use cases. They can be either point-in-time (snapshot) or continuous time (animated). Snapshot views typically have lower-stress data-retrieval requirements and are designed to help users make quick decisions visually through rapid assimilation of visual data. Animated views are designed to show real-time status or trends, and typically will have more demanding data-retrieval requirements.

interest is a patient named "Charles Kramer," and the user wishes to see a display of "online entities displayed by clinical relevance and recency of touch." A clinical information system adapter 104 provides a set of activities related to clinical relevance. For illustrative purposes, assume the activities include the number of orders placed by an entity element against Charles Kramer (MedOrder), documents authored or edited by an entity element for Charles Kramer (DocAuthored), and number of times the chart was opened by a particular entity element for Charles Kramer (ChartOpen). Since the system in this example is to display "online entities," the system will also filter based on presence status so a real-time collaboration system adapter 104 is also needed.

These two adapters 104 provide raw information, which is then grouped together by entity element as shown at 204, with an excerpt shown in Table 1. Table 1 displays the entity elements and a unique identifier associated with each entity element. It also shows the activity type, date and a property value, if applicable.

TABLE 1

Excerpt of the "Touch Collection" following the Aggregation Phase.

| Entity Element | Unique Id | Activity Type | Date | Property Value |
|---|---|---|---|---|
| Paige Kaeding | PK12345-123 | ChartOpen | 20030101-1715 | |
| Paige Kaeding | PK12345-123 | ChartOpen | 20030102-1915 | |
| Paige Kaeding | PK12345-123 | ChartOpen | 20030103-2037 | |
| Paige Kaeding | PK12345-123 | ChartOpen | 20030105-1843 | |
| Paige Kaeding | PK12345-123 | ChartOpen | 20030105-2304 | |
| Paige Kaeding | PK12345-123 | DocAuthored | 20030101-1720 | |
| Paige Kaeding | PK12345-123 | DocAuthored | 20030102-1935 | |
| Paige Kaeding | PK12345-123 | DocAuthored | 20030103-1900 | |
| Paige Kaeding | PK12345-123 | DocAuthored | 20030105-2330 | |
| Paige Kaeding | PK12345-123 | Presence | 20030106-0005 | Online |
| Paige Kaeding | PK12345-123 | Role | 20030106-0005 | R.N. |
| J Billings | JB56789-435 | MedOrder | 20030101-1212 | |
| J Billings | JB56789-435 | MedOrder | 20030101-1212 | |
| J Billings | JB56789-435 | ChartOpen | 20030102-1245 | |
| J Billings | JB56789-435 | DocAuthored | 20030102-1300 | |
| J Billings | JB56789-435 | Presence | 20030106-0005 | Online |
| J Billings | JB56789-435 | Role | 20030106-0005 | Admitting MD |
| Leah Phelan | LP45455-909 | ChartOpen | 20030104-1414 | |
| Leah Phelan | LP45455-909 | Presence | 20030106-0005 | Offline |
| Leah Phelan | LP45455-909 | Role | 20030106-0005 | R.N. |
| ... | | | | |

Exemplary Display Generation

The following simplified textual example illustrates the method of the present invention showing how entity element information is accumulated and turned into a visualization or display. For clarity, this example shows the generation of a snapshot view, with commentary at appropriate times for variations for multiple frames.

Under the first step shown at 202, originating system adapters 104 collect entity element information and their properties from originating systems 102. In this example, the entity of If the user in this example does not care about entity elements who are offline, the system can filter those out immediately, as shown at 206. Note that the system may also filter out data in the adapters 104, rather than after the list is generated in step 204. Table 2 shows an excerpt of the combined data after Leah Phelan (the offline entity element) has been filtered out based on the "Property Value" associated with the Presence activity type. After this filtering stage, "Property Value" information can be stored directly with the entity element.

TABLE 2

Elements and Associated Properties after Exclusionary Filtering.

| Entity Element | Unique Id | Activity Type | Date | Property Value |
|---|---|---|---|---|
| Paige Kaeding | PK12345-123 | ChartOpen | 20030101-1715 | |
| Paige Kaeding | PK12345-123 | ChartOpen | 20030102-1915 | |
| Paige Kaeding | PK12345-123 | ChartOpen | 20030103-2037 | |

TABLE 2-continued

Elements and Associated Properties after Exclusionary Filtering.

| Entity Element | Unique Id | Activity Type | Date | Property Value |
|---|---|---|---|---|
| Paige Kaeding | PK12345-123 | ChartOpen | 20030105-1843 | |
| Paige Kaeding | PK12345-123 | ChartOpen | 20030105-2304 | |
| Paige Kaeding | PK12345-123 | DocAuthored | 20030101-1720 | |
| Paige Kaeding | PK12345-123 | DocAuthored | 20030102-1935 | |
| Paige Kaeding | PK12345-123 | DocAuthored | 20030103-1900 | |
| Paige Kaeding | PK12345-123 | DocAuthored | 20030105-2330 | |
| Paige Kaeding | PK12345-123 | Presence | 20030106-0005 | Online |
| Paige Kaeding | PK12345-123 | Role | 20030106-0005 | R.N. |
| J Billings | JB56789-435 | MedOrder | 20030101-1212 | |
| J Billings | JB56789-435 | MedOrder | 20030101-1212 | |
| J Billings | JB56789-435 | ChartOpen | 20030102-1245 | |
| J Billings | JB56789-435 | DocAuthored | 20030102-1300 | |
| J Billings | JB56789-435 | Presence | 20030106-0005 | Online |
| J Billings | JB56789-435 | Role | 20030106-0005 | Admitting MD |
| ... | | | | |

During the next step shown at 208, frequencies of the relevant activities are calculated and summarized into either a single frame (for a static, snapshot view) or into multiple frames (for an animated view). Since the weighting algorithms used in step 210 in this example use the number of days an entity element interacted with the element of interest, the system in this example also calculates a count of "DaysTouched." Using the example data above for a snapshot view, Table 3 shows the calculated frequencies.

TABLE 3

Calculated Frequencies

| Entity Element | Unique Id | Activity Type | LastDate | Frequency |
|---|---|---|---|---|
| Paige Kaeding | PK12345-123 | ChartOpen | 20030105-2304 | 5 |
| Paige Kaeding | PK12345-123 | DocAuthored | 20030105-2330 | 4 |
| Paige Kaeding | PK12345-123 | DaysTouched | 20030105-2330 | 4 |
| J Billings | JB56789-435 | MedOrder | 20030101-1212 | 2 |
| J Billings | JB56789-435 | ChartOpen | 20030102-1245 | 1 |
| J Billings | JB56789-435 | DocAuthored | 20030102-1245 | 1 |
| J Billings | JB56789-435 | DaysTouched | 20030102-1245 | 2 |
| ... | | | | |

Role information and Presence information, being properties uniquely assigned to an individual, are not included in the frequencies. The system and method of the present invention may be used as an interactive practice tool. Additionally, the system and method may be used to view clinical and social relationship information over time through an animated view mode. For an animation view of a particular overall time period, these frequencies would be counted for a particular range of events (called a range window), corresponding to a set time period (e.g., a sliding window of forty-eight hours) or corresponding to a set number of activity events (e.g., the last fifty touches). Frequencies are then subsequently recounted for a sliding range window corresponding to an advancement of the range window by a "step" size, indicating by how much time (or by how many activity events or touches) the range window should be advanced before recalculation. The range window and step size parameters are defined as part of the visualization. For example, a range window may be defined as "all touches occurring in a given twenty-four hour time period", with a step size set to twenty-four hours, and the overall time period being the last thirty days. This would produce thirty frames, corresponding to a sequence of twenty-four hour range window snapshots calculated every twenty-four hours for the past thirty days. The animation view of the frames may illustrate changes in the nature of the relationship over time.

In the next step shown at 210, clinical relevance scores are calculated to generate relevance perspectives. In general, for this example, the clinical relevance algorithm is:

SUM (frequency_of_feature[i]*weight_of_feature[i])* (scaling_factor): where scaling_factor normalizes the weighted sum to a given patient-specific context (e.g., DaysTouched/TotalDays).

Depending on the particular use, the type of activity types used in the algorithm and the weight applied to each activity type can be adjusted. For example, if a user wants to determine who has the most interaction with the patient, the frequency of touches is more important than the nature of touches, and the weights applied to particular activity types will be roughly the same. If the user wants to determine the decision maker with the most responsibility for the patient's health status, the nature of touches becomes important, and the more direct and invasive activity types are given higher weights than indirect and passive active types.

In this example, if the user is interested in identifying the key decision maker, the visualization filter rule of interest is "decision making" relevance. In addition, if the user is interested in the how recently an entity element has had contact with the entity of interest, the "recency of touch" is relevant. The "decision making" relevance filter is frequency based, while "recency of touch" is a simple time-based visualization rule. The system loads the "decision making" relevance filter weights and applies the following weighting factors:

MedOrder=25, ChartOpen=2, DocAuthored=3.

In addition, "days touched" is used to scale these values based on the total days of interest (for this example, Jan. 1, 2003 through Jan. 6, 2003, or 6 days.) Because "recency of touch" is a simple rule, there are no weights associated with it. So the system simply determines the most recent event and passes the time stamp along. Since only one frame is desired in this example, the system can generate the clinical relationship scores and relevance perspectives vectors by applying the weights to the collected statistics as follows with the results shown in Table 4.

Paige Kaeding scores:

[(0*25)+(5*2)+(4*3)]*(⅙)=14.67

J Billings scores:

[(2*25)+(1*2)+(1*3)]*(⅔)=18.33

TABLE 4

Relevance Perspectives

| Entity Element | Unique Id | Relevance Class | Socre | RecencyOfTouch |
|---|---|---|---|---|
| Paige Kaeding | PK12345-123 | DecisionMaking | 14.67 | 20030105-2330 |
| J Billings | JB56789-435 | DecisionMaking | 18.33 | 20030102-1245 |

Once again, for an animation view, these calculations would be made on a per-frame basis, respecting the epoch and step values mentioned earlier.

Next, as shown at 212, once the URL is invoked, the visualization model is complete and includes the following information: the entities that will be displayed; the relevance classes that will be displayed; the appropriate clinical relationship scores to be displayed for each relevance class; additional property information about the entity elements; and frames that can fulfill the visualization of animated presentations of the data.

In this example, the entity elements are Paige Kaeding and J Billings, the relevance perspectives are "decision making" and "recency of touch," clinical reference values have been generated for each, and the additional property information includes role and presence status.

As shown at 214, the next step involves instantiating the appropriate visualization adapter in engine 108 (e.g., "Graph Mode for Scalable Vector Graphics or SVG", or "table mode for HTML"). Based on the context of the request (e.g., from a web page requiring an interactive applet, from a Java Server Page requiring a simple PNG graphic file), different visualization adapters may be invoked to render a display appropriate for the venue, as would be understood by one of skill in the art.

Figure 3:
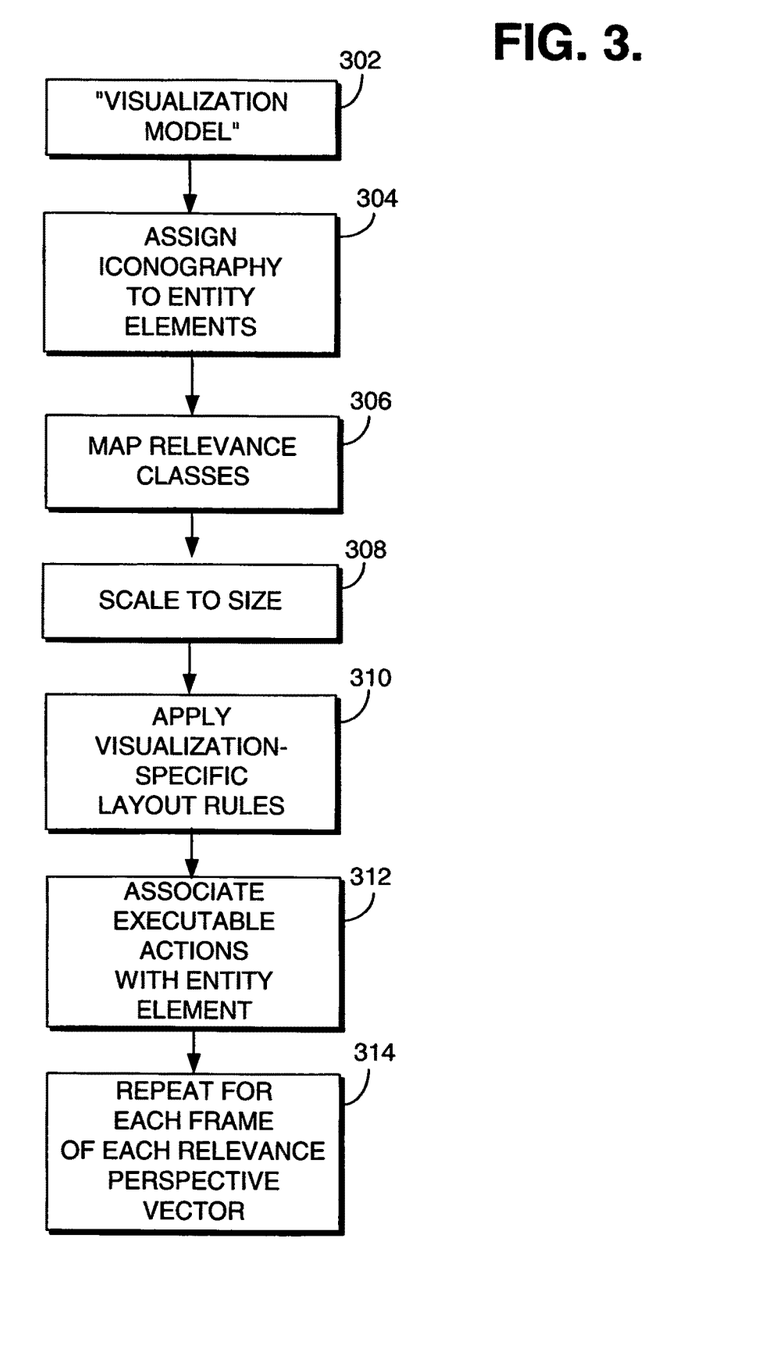
FIG. 3 is a flowchart detailing the steps carried out by the visualization engine component of the present invention.

FIG. 3 gives a detailed flow of the operation of visualization engine 108. This is a general method of how one might implement a visualization adapter in engine 108. Depending on the venue, certain steps may not be appropriate. For example, if a tabular view is used, it may be unnecessary to associate iconography with each entity element.

As shown at 304, the process of the visualization engine 108 begins when the visualization model 302 is taken and iconography is assigned to each entity element. The iconography assigned to each entity element can be based on any entity property such as role and/or presence status. Next, relevance classes are mapped to a visual layout representation, as shown at 306. For example, "DecisionMaking" relevance could be mapped by the size of the icon, "RecencyOfTouch" could be mapped by the proximity of the entity element node to the entity of interest node, and the Presence status could be mapped by the color of the entity element node. For size and positional mapped relevance classes, the entity element nodes can be scaled to size for the target area that is available, as shown at 308. This step may be required to ensure that the entity element nodes fit within the given target area or to ensure that the relative scale is maintained between the various entity element nodes. Next, as shown at 310, visualization-specific layout rules are applied. Under this step, geometric positioning is applied to minimize the overlap of entity element nodes on the screen or the entity elements are sorted for a tabular display. Executable actions are then associated with each entity element, as shown at 312. For animated views, steps 308 through 312 are repeated for each frame to be generated, as shown at 314.

Figure 4:
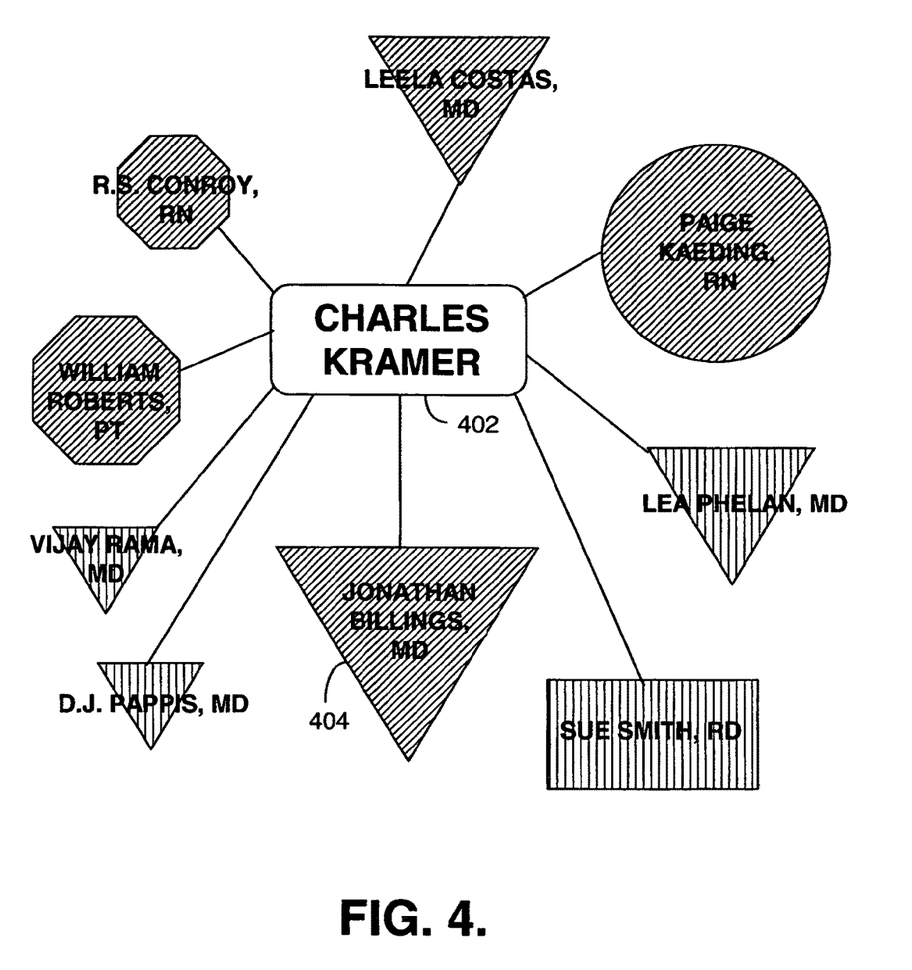
FIGS. 4-6 are screen shots illustrating exemplary visualizations generated by the system.
Figure 5:
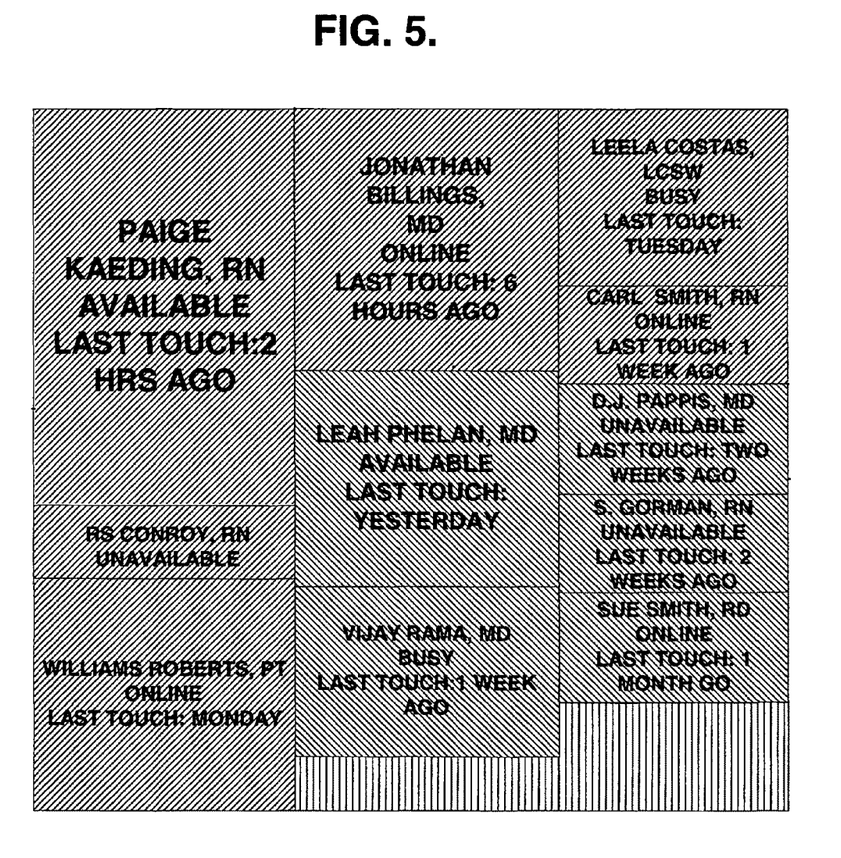

FIGS. 4-5 are examples of schematic screen shots of the generated visualizations. FIG. 4 illustrates one graphical visualization based on the previous example. In FIG. 4, each entity element is represented as an entity element node 404 surrounding the entity of interest node 402. The shape of each entity element node represents the entity element's role. For example, each doctor is represented as a triangle. The size of the entity element node represents the "DecisionMaking" relevance. Here, Jonathan Billings and Paige Kaeding are of higher relevance in decision making. The color or shading of the entity element node represents the presence status of the entity element. For example, red could indicate that the entity element is unavailable, yellow could indicate that the entity element is busy, and green could indicate that the entity element is available. Although shown with different shading, color is preferred. The length of the line between the entity of interest and each entity represents the "recency of touch." Each of these parameters (i.e. shape, size, color, length of line) can be modified to represent a different entity element property or relevance class.

FIG. 5 illustrates an alternative graphical form of display for the preceding example. The location of the entity element represents "recency of touch." In this exemplary screen shot, the entities with the more recent touches are located toward the upper-left corner. The size of each entity element's box represents the "decision making" relevance. The color or shading of each entity element's box represents each entity element's presence status. Again, although shown with different shading, color is preferred. As in FIG. 4, each of the parameters (i.e. location, size, and color) can be modified to represent a different entity element property or relevance class.

Figure 6:
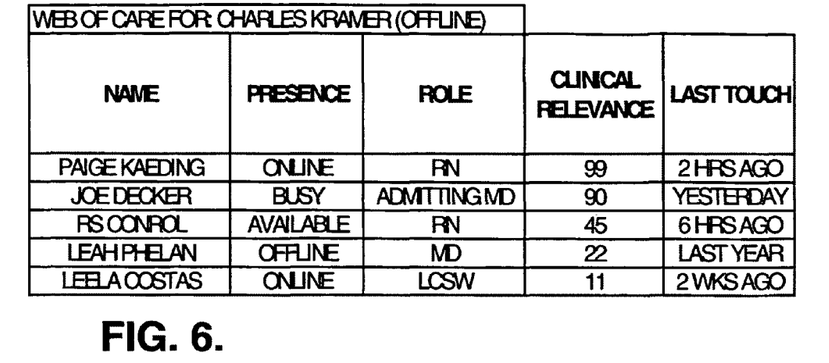

FIG. 6 illustrates another visualization based on the previous example. In this screen shot, the entity elements are grouped together in a tabular form. The Presence values, the clinical relevance values, and the values for the "recency of touch" are included in the table. The names are preferably sorted in order of clinical relevance and are actionable. Additional variations are also contemplated. By way of example, the Presence values may be represented by iconography associated with the names.

The example given above, as well as the displays shown in FIGS. 4-6, are merely exemplary. It should be understood that these examples are not meant in any way to be limiting. A myriad of visualization displays and screen shots are possible utilizing the visualization model, and are all contemplated by the present invention. It can be seen that the visualization displays created and shown in FIGS. 4-6 quickly and efficiently illustrate clinical relationship information. Moreover, when the action classes are associated with the iconography, a useful interactive display is created. For example, executable actions can be used to allow a user to select particular icons shown in FIG. 4 to initiate a real time collaboration session with desired entities.

Those skilled in the art will appreciate that the present invention represents a significant advancement of the state of the art beyond existing applications, especially with respect to the practical benefits it provides. The present invention provides a logical model and means of display for clinically-relevant relationships gleaned from one or more sources. The present invention also provides a mechanism for weighting the parameters of clinical relevance to change the display to highlight clinical relevance as defined for difference purposes. In addition, the present invention includes an interactive graphical interface that makes the visualization capable of being used as a launch point for various application activities ranging from specific things, such as initiating a collaboration session with the most appropriate people, to navigating the clinical network. Furthermore, the model and display are capable of being merged and intersected, meaning that it is possible to get a broader view by combining multiple models and displays together into a single, large display. Thus, the system can be used for a variety of functions including initiating collaboration, managing person-personnel security and care team relationships, and for infection control purposes.

Alternative embodiments and implementations of the present invention will become apparent to those skilled in the art to which it pertains upon review of the specification, including the drawing figures. For example, any of a number of relevance algorithms may be employed to generate a relevance score. Accordingly, the scope of the present invention is defined by the appended claims rather than the foregoing description.

What is claimed is:

1. One or more non-transitory computer-storage media having computer-executable instructions stored thereon that, when executed, perform a method in a computer system of generating a visualization model used to display clinical relationships between a plurality of physical entity elements and a physical entity of interest, the method comprising:
    retrieving properties for each of the entity elements and the entity of interest, the properties including at least one activity type indicative of clinical contact between each of the entity elements and the entity of interest;
    calculating a frequency for the at least one activity type, wherein the frequency is a quantity of times the at least one activity type is performed by each entity element;
    weighting the at least one activity type based on a desired clinical relevance, wherein the desired clinical relevance represents clinical decision-making ability of each entity element where entity elements with clinical decision-making relevance are identified as being associated with directly physical and invasive activity types including performing a healthcare procedure on the entity of interest rather than indirect activity types including opening a chart associated with the entity of interest;
    calculating a clinical relevance score for each entity element based on the at least one activity type, the frequency for the at least one activity type, and the weight of the at least one activity type; and
    generating a visualization model using the retrieved properties of each entity element and the calculated clinical relevance scores, the model representing the clinical relationship and clinical relevance of each entity element relative to the entity of interest.

2. The one or more computer-storage media of claim 1, further comprising combining the retrieved properties and sorting by entity element after the properties are retrieved.

3. The one or more computer-storage media of claim 1, further comprising filtering the retrieved properties to eliminate any properties that are not of interest.

4. The one or more computer-storage media of claim 1, further comprising repeating the retrieving, calculating and generating steps for each of a plurality of time periods.

5. The one or more computer-storage media of claim 1, wherein the relationships are clinical relationships, the entity of interest is an individual receiving healthcare and the entity elements are individuals providing the healthcare or resources for providing healthcare.

6. The one or more computer-storage media of claim 1, further comprising displaying, on a display device, the visualization of the relationships using the generated visualization model.

7. The one or more computer-storage media of claim 6, further comprising assigning icons to each of the displayed entity elements.

8. The one or more computer-storage media of claim 7, wherein the size, shape and color of the assigned icons are used to convey relevance and property information.

9. The one or more computer-storage media of claim 7, further comprising associating at least one executable action with at least one of the entity elements.

10. The one or more computer-storage media of claim 7, wherein the executable action is an executable uniform resource locator (URL) that is executed by a mouse click on the entity icon.

11. The one or more computer-storage media of claim 1, wherein the contact between the entity element and the entity of interest is an actual physical contact.

12. The one or more computer-storage media of claim 1, wherein the contact between the entity element and the entity of interest is a request that will direct a physical contact between an entity element and the entity of interest.

13. The one or more computer-storage media of claim 1, wherein the contact between the entity element and the entity of interest is a passive contact between the entity element and the entity of interest.

14. A computer system for generating a patient focused visualization to display clinical relationships between the patient and a plurality of healthcare providers, along with a clinical relevance of the entity elements to the entity of interest, the system comprising:
    at least one computing device associated with one or more processors;
    at least one originating system adapter component that retrieves properties of healthcare providers that have had clinical contact with the patient during the patient's course of treatment from an originating system, the properties including at least one activity type indicative of clinical contact between the healthcare provider and the patient;
    a visualization model generation component that calculates a clinical relevance score for each healthcare provider based on a clinical relevance algorithm and the at least one activity type indicative of contact between each healthcare provider and the patient, wherein the clinical relevance algorithm utilizes the at least one activity type, a weight value of the at least one activity type, and a quantity of times that the at least one activity type is performed by each healthcare provider for the patient during the patient's course of treatment; and
    a visualization engine that generates a visualization using the retrieved properties of each healthcare provider and the clinical relevance score calculated for each healthcare provider,
    wherein the visualization model and the visualization engine utilize real-time data to generate the visualization as an animation, where the clinical relevance score is calculated per each frame of the animation.

15. The computer system of claim 14, further comprising a filter component that operates to remove unwanted properties from the retrieved properties prior to the calculation of the relevance score.

16. The computer system of claim 14, wherein a plurality of originating systems are available, further comprising an originating system adapter for each available originating system.

17. The computer system of claim 14, wherein the visualization engine also assigns iconography to the healthcare provider to be displayed and associates action classes with each healthcare provider.

18. The computer system of claim 14, wherein the contact between the healthcare providers and the patient is indirect contact.

19. A user interface stored on a non-transitory computer readable medium and executable on a computer, comprising:
    an patient entity of interest icon; and
    a plurality of entity element icons, each representing an entity element associated with the entity of interest, wherein each entity element icon has associated therewith an executable action,
    and wherein the arrangement of the entity element icons relative to the entity of interest icon conveys information about a clinical relationship between the entity of interest and each entity element based on one or more clinical contacts between the entity of interest and each entity element such that the arrangement represents a clinical relevance score of each entity element based on a plurality of activities, and wherein each of the plurality of activities are associated with a weight value according to a type of each of the plurality of activities, and wherein the one or more clinical contacts are performed between a healthcare provider and a patient during the patient's course of treatment,
    and wherein the user interface is generated by a visualization engine utilizing the clinical relevance score of each entity element relative to the entity of interest,
    and wherein the user interface is continuously updated and animated such that a real-time status is displayed, wherein the clinical relevance score is calculated per each frame of the animation.

20. The user interface of claim 19, wherein the relationship information is conveyed using the color, shape and positioning of the entity element icons.

21. The user interface of claim 20, wherein the executable action is a uniform resource locator (URL) unique to the entity element with which it is associated.

22. The user interface of claim 21, wherein the entity element icons represent healthcare resources and wherein the entity of interest icon represents a person receiving healthcare.

23. One or more non-transitory computer-storage media having computer-executable instructions stored thereon that, when executed, perform a method in a computer system of generating a visualization model used to display clinical relationships between a plurality of healthcare providers and a patient, the method comprising:
    retrieving properties for each of the healthcare providers relative to the patient for a plurality of time periods, the properties associated with one or more physical clinical contacts between each healthcare provider and the patient during the patient's course of treatment, wherein the plurality of time periods is a predetermined length of time including a range window and an overall time period for which to calculate a recency-of-touch value for each healthcare provider, wherein the recency-of-touch value is a recency of clinical interactions between each healthcare provider and the patient;
    generating a visualization model representing the clinical relationship and clinical relevance of each healthcare provider relative to the patient using the retrieved properties of each healthcare provider for each time period, wherein the clinical relevance is calculated based on both a decision-making ability of each healthcare provider and the recency-of-touch value of healthcare provider, wherein the decision-making ability is based on whether a type of clinical interaction is a direct clinical interaction or an indirect clinical interaction, a direct clinical interaction having a weight value associated with the direct clinical interaction that is higher than the weight value associated with the indirect clinical interaction; and
    sequentially displaying the clinical relationships using the generated visualization model for each time period such that the clinical relationships are displayed in an animated view and calculations to determine the clinical relationships are calculated per each frame of the animation.

24. The one or more computer-storage media of claim 23, wherein the clinical relevance of each healthcare provider relative to the patient is determined by calculating a relevance score for each healthcare provider using the retrieved properties of each healthcare provider, the relevance score weighting certain properties above others to rank each healthcare provider's relevance to the patient.

25. The one or more computer-storage media of claim 24, further comprising filtering the retrieved properties to eliminate any properties that are not of interest.

26. The one or more computer-storage media of claim 23, wherein the relationships are clinical relationships and the patient is an individual receiving healthcare.

* * * * *